United States Patent
Leise, III

(10) Patent No.: US 10,485,893 B2
(45) Date of Patent: Nov. 26, 2019

(54) ANTIMICROBIAL HYDROCOLLOID DRESSING CONTAINING SEQUESTERED PEROXIDE AND PREPARATION THEREOF

(71) Applicant: Sarasota Medical Products, Inc., Sarasota, FL (US)

(72) Inventor: Walter F. Leise, III, Sarasota, FL (US)

(73) Assignee: Sarasota Medical Products, Inc., Sarasota, FL (US)

( * ) Notice: Subject to any disclaimer, the term of this patent is extended or adjusted under 35 U.S.C. 154(b) by 187 days.

(21) Appl. No.: 14/540,911

(22) Filed: Nov. 13, 2014

(65) Prior Publication Data

US 2016/0136323 A1 May 19, 2016

(51) Int. Cl.
| | |
|---|---|
| *A61L 26/00* | (2006.01) |
| *A61L 24/00* | (2006.01) |
| *A61L 24/02* | (2006.01) |
| *A61L 15/18* | (2006.01) |
| *A61L 15/58* | (2006.01) |
| *A61L 24/04* | (2006.01) |
| *C09J 123/22* | (2006.01) |

(52) U.S. Cl.
CPC .......... *A61L 26/0004* (2013.01); *A61L 15/18* (2013.01); *A61L 15/58* (2013.01); *A61L 15/585* (2013.01); *A61L 24/0015* (2013.01); *A61L 24/0031* (2013.01); *A61L 24/02* (2013.01); *A61L 24/043* (2013.01); *A61L 26/008* (2013.01); *A61L 26/0052* (2013.01); *A61L 26/0066* (2013.01); *C09J 123/22* (2013.01); *A61L 2300/11* (2013.01); *A61L 2300/404* (2013.01)

(58) Field of Classification Search
CPC ............... A61L 26/0004; A61L 26/004; A61L 24/0015; A61L 26/0066; A61L 26/0052; A61L 24/02; A61L 26/008; A61L 15/18; A61L 15/585; A61L 24/043; A61L 24/0031; A61L 15/58; A61L 2300/11; A61L 2300/404; C09J 123/22
See application file for complete search history.

(56) References Cited

U.S. PATENT DOCUMENTS

| | | | |
|---|---|---|---|
| 3,339,546 A | 9/1967 | Chen | |
| 3,612,053 A | 10/1971 | Pratt | |
| 4,166,051 A | 8/1979 | Chen | |
| 4,184,635 A | 1/1980 | Bloomfield | |
| 4,192,785 A | 3/1980 | Chen | |
| 4,201,211 A * | 5/1980 | Chandrasekaran et al. | .. 424/448 |
| 4,231,369 A | 11/1980 | Sorensen et al. | |
| 4,393,080 A | 7/1983 | Pawelchak et al. | |
| 4,393,150 A | 7/1983 | Kreener | |
| 4,496,357 A | 1/1985 | Osburn | |
| 4,743,499 A | 5/1988 | Volke | |
| 5,492,943 A | 2/1996 | Stempel | |
| 5,554,106 A | 9/1996 | Layman-Spiller et al. | |
| 5,569,207 A | 10/1996 | Gisselbeg et al. | |
| 6,143,798 A | 11/2000 | Jensen et al. | |
| 6,468,521 B1 | 10/2002 | Pedersen et al. | |
| 6,884,920 B2 | 4/2005 | Worthley | |
| 2006/0121100 A1 * | 6/2006 | Opremcak | ..................... 424/445 |
| 2010/0247615 A1 | 9/2010 | Toreki et al. | |
| 2011/0171280 A1 * | 7/2011 | Toreki | ................... D06M 11/155 |
| | | | 424/411 |

FOREIGN PATENT DOCUMENTS

| | | | | |
|---|---|---|---|---|
| EP | 0 130 061 A1 | 1/1985 | | |
| JP | S60-020976 A | 2/1985 | | |
| JP | S62-042920 A | 2/1987 | | |
| JP | 2004505729 A | 2/2004 | | |
| JP | 2008-529917 A | 8/2008 | | |
| JP | 2012518062 A | 8/2012 | | |
| JP | 2013527327 A | 6/2013 | | |
| WO | WO87/03477 | * | 6/1987 | ............... A61K 9/00 |
| WO | 02/13879 A2 | 2/2002 | | |
| WO | 2006088749 A2 | 8/2006 | | |
| WO | 2010/144503 A2 | 12/2010 | | |
| WO | 2012/134770 A1 | 10/2012 | | |

OTHER PUBLICATIONS

Avery Dennison, "New Gentle Hydrocolloid Pressure Sensitive Adhesives for Wound Care", pp. 1-8, Accessed Dec. 1, 2017.*
European Search Report issued in European Patent Application No. 15 19 4510, dated Mar. 16, 2016, 9 pages.
Notification of Reasons for Refusal and English Translation issued in Japanese Patent Application No. 2015-221864, dated Oct. 6, 2016, 8 pages.
First Office Action and English Translation issued in Chinese Patent Application No. 201510780205.0, dated Mar. 6, 2017, 14 pages.
Notice of Reasons for Refusal and English Translation issued in Japanese Patent Application No. 2015-221864, dated Jun. 6, 2017, 6 pages.
Notification of Reasons for Refusal issued in corresponding Japanese Application No. 2015-221864, dated Feb. 5, 2019, 18 pages.

* cited by examiner

Primary Examiner — Rachael E Bredefeld
(74) Attorney, Agent, or Firm — Quarles & Brady LLP

(57) ABSTRACT

This disclosure provides for an antimicrobial pressure sensitive adhesive composition that includes a sequestered peroxide source and devices that incorporate such a composition.

9 Claims, 4 Drawing Sheets

ANTIMICROBIAL HYDROCOLLOID DRESSING CONTAINING SEQUESTERED PEROXIDE AND PREPARATION THEREOF

CROSS REFERENCE TO RELATED APPLICATIONS

Not Applicable

REFERENCE REGARDING FEDERALLY SPONSORED RESEARCH AND DEVELOPMENT

Not Applicable

SEQUENCE LISTING

Not Applicable

BACKGROUND

Field of the Disclosure

The present disclosure is related to advanced wound care, incontinence care, catheter securement, and ostomy devices to be attached to a human body through an adhesive. The adhesive is a biomedical polymer material that incorporates sequestered peroxide as an antimicrobial agent.

Description of the Related Art

Advanced wound care, incontinence care, and ostomy care devices are well known in the market place. Typically, these devices are attached via a skin friendly adhesive, such as a hydrocolloid, acrylic, silicone, etc.

For example, U.S. Pat. No. 4,551,490 discloses pressure sensitive adhesive compositions particularly adapted for use in the fields of incontinence, ostomy care, wound care, and burn care dressings. Similarly, other prior art devices such as those described in U.S. Pat. Nos. 3,339,546, 3,612,053, 4,166,051, 4,184,635, 4,192,785, 4,231,369, 4,393,150, 4,393,080, 4,496,357, 4,743,499, 5,492,943, and 6,143,798, also disclose such compositions as well.

Superabsorbent materials comprising peroxide are disclosed in U.S. Pub. No. 2010/0247615. This publication pertains to a polymeric composition and an antimicrobial composition that combine to form an antimicrobial superabsorbent polymer used within diapers and other sanitary products.

Antimicrobial pressure sensitive adhesives and the uses thereof are also well known and described in U.S. Pat. Nos. 5,569,207, 5,681,579, 6,468,521, 5,554,106, and 6,884,920.

SUMMARY

The present disclosure is based on the discovery that peroxides bound to polymers, oligomers, and/or matrices can maintain antimicrobial efficacy, and that these substrates act as stabilizers of the peroxide species. Therefore, the peroxide concentrations can be significantly reduced, thus minimizing deleterious effects normally found when applying a peroxide to an open wound. In addition, these stabilized and active peroxide species can be formulated with typical hydrocolloid materials to produce skin friendly pressure sensitive adhesives to minimize the bioburden within the adhesive and provide a hygienic environment.

In general, the antimicrobial hydrocolloid laminate in the present disclosure includes an extruded mass of adhesive between two or more substrates, release liners, or laminated liners. The subsequent intermediate is converted, cut, or transformed to create antimicrobial wound care dressings, wound care foams, ostomy devices, incontinence adhesives, devices which secure catheters, and the like.

In one aspect, an antimicrobial pressure sensitive adhesive composition includes a sequestered peroxide source.

In another aspect, an adhesive device includes an adherent material having an amount of peroxide. The amount of peroxide is sufficient to provide at least 0.05% active peroxide within the adherent material.

In a third aspect, a pressure sensitive adhesive composition includes about 2% to about 45% by weight of one or more polyisobutylenes or a blend of one or more polyisobutylenes and butyl rubber, about 0.01% to about 40% by weight of mineral oil, about 1.0% to about 30% by weight of one or more styrene radial or block type copolymers, about 10% to about 65% by weight of one or more water soluble hydrocolloid gums, up to about 15% by weight of one or more water swellable cohesive strengthening agents, about 2.5% to about 20% by weight of a tackifier, about 0.01% to about 30% by weight of a super absorbent polymer, about 0.01% to about 10% by weight of a metal salt, about 0.01% to about 2.0% by weight of an antioxidant, and about 0.01% to about 10% by weight of a peroxide. The water soluble hydrocolloid gum and the water swellable cohesive strengthening agent together are present at about 15% to about 65% by weight of the composition.

BRIEF DESCRIPTION OF THE DRAWINGS

Figures 1A, 1B, 1C, 1D, 1E, 1F:
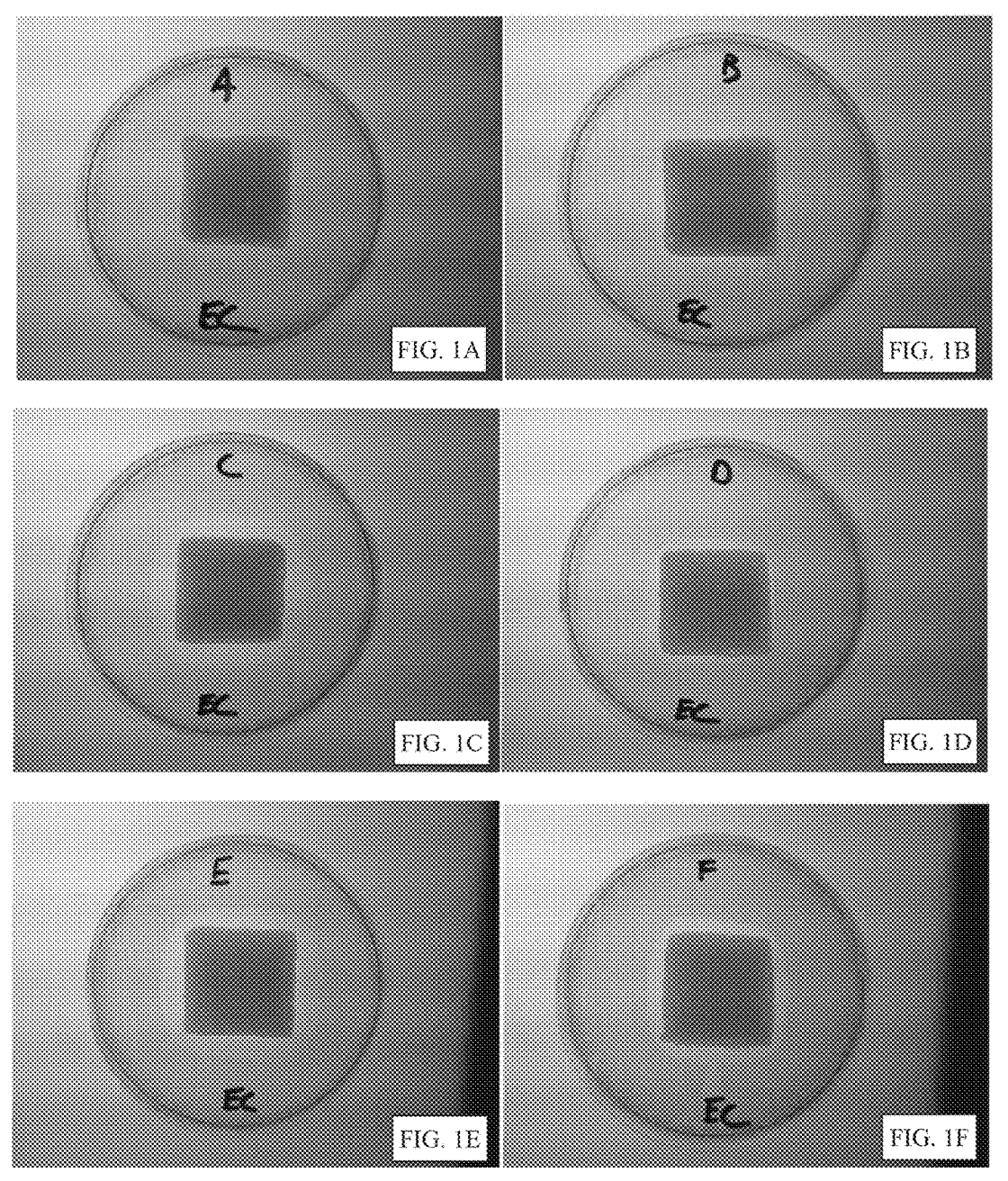

FIGS. 1A-F depict results of a 1" adhesive patch (30 mil thick) placed on a plate coated with E. coli to test the zone of inhibition caused thereby, of which, FIG. 1A=a 0.05% peroxide in the adhesive formulation, FIG. 1B=a 0.10% peroxide in the adhesive formulation, FIG. 1C=a 0.20% peroxide in the adhesive formulation, FIG. 1D=a 0.40% peroxide in the adhesive formulation, FIG. 1E=a 0.80% peroxide in the adhesive formulation, and FIG. 1F=a 2.00% peroxide in the adhesive formulation;

DETAILED DESCRIPTION

Figure 2A:
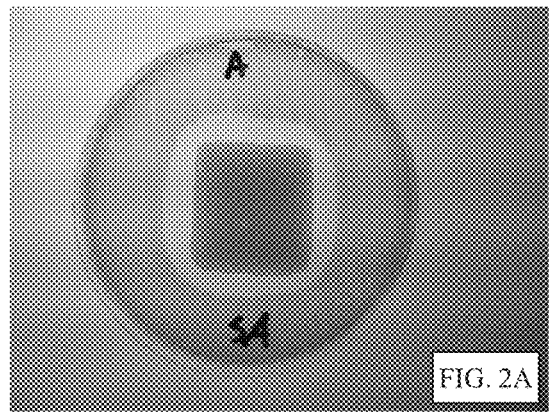
FIGS. 2A-F depict results of a 1" adhesive patch (30 mil thick) placed on a plate coated with MRSA to test the zone of inhibition caused thereby, of which, FIG. 2A=a 0.05% peroxide in the adhesive formulation, FIG. 2B=a 0.10% peroxide in the adhesive formulation, FIG. 2C=a 0.20% peroxide in the adhesive formulation, FIG. 2D=a 0.40% peroxide in the adhesive formulation, FIG. 2E=a 0.80% peroxide in the adhesive formulation, and FIG. 2F=a 2.00% peroxide in the adhesive formulation.
Figure 2B:
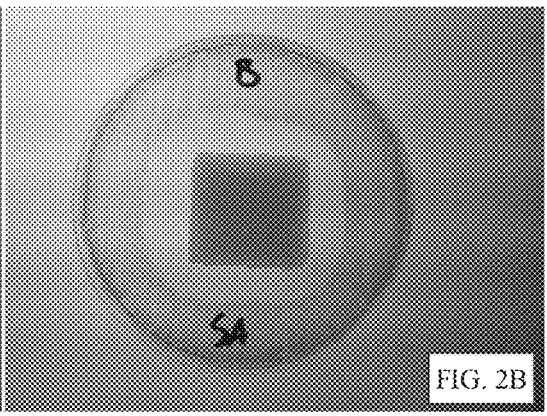
Figure 2C:
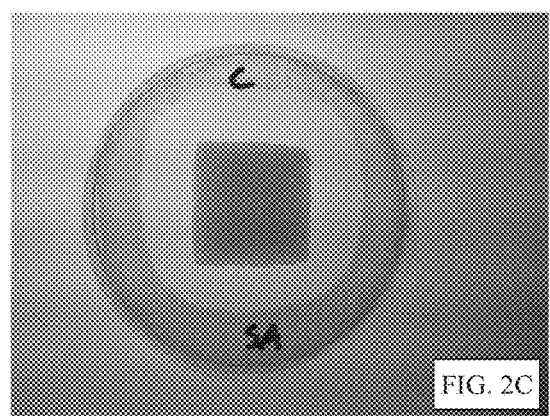
Figure 2D:
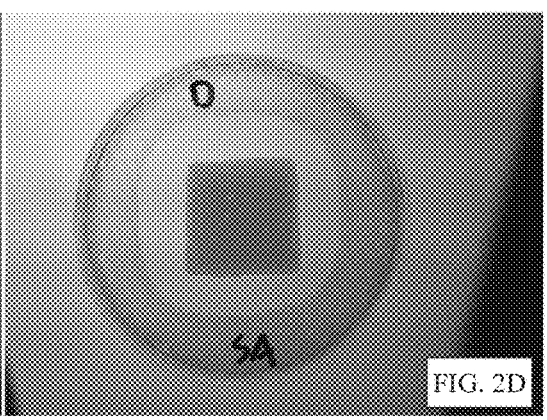
Figure 2E:
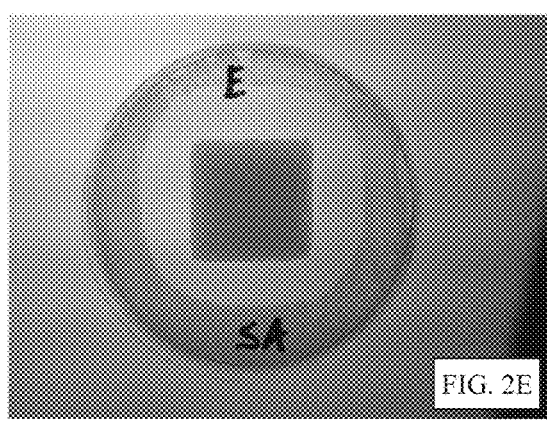
Figure 2F:
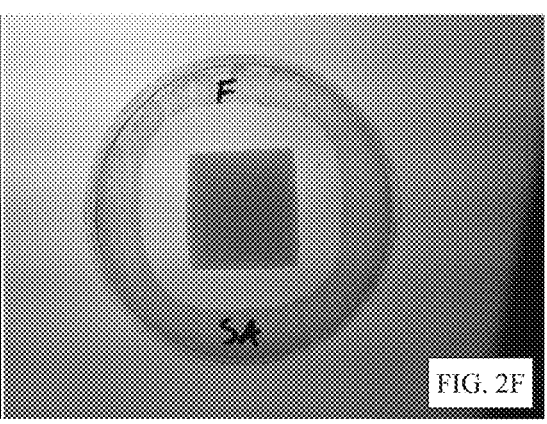

There are many well-known prior art antimicrobial adhesive compositions for wounds that reduce microbial proliferation and reduce hospital acquired infections, such as those including antiseptics and disinfectants. However, the present disclosure provides for compositions of pressure sensitive adhesives that contain sequestered and stable peroxides. These new compositions may be used with advantageous results as an antimicrobial pressure sensitive adhesive, a wound treatment, such as a hydrocolloid dressing or foam dressing, and/or an antimicrobial treatment for ostomy and incontinence applications.

The wound bed itself offers an attractive environment in which bacteria and other microbes can flourish, which complicates normal wound healing. Therefore, managing a wound with antibiotics or antimicrobials to minimize infection would be a logical treatment. However, there are many potential and adverse effects associated with the clinical use of antibiotics and antimicrobials, such as allergic reactions, heavy metal poisoning, and destruction of proliferating tissue, which can result in slow wound closure and other complications. The degree to which these adverse effects may be realized is usually dependent on the concentration of the antimicrobial agent administered. One important adverse side effect of antibiotics is the emergence of antibiotic resistant microorgansisms, MRSA for example. The emergence of antibiotic-resistant pathogens is a serious threat to controlling infections and provides a convincing reason to develop new therapies designed to effectively prevent and treat bacterial infections.

Some antimicrobial treatments include silver-containing gels, compounds containing heavy metals, solutions of hydrogen peroxide, and other natural substances. Silver ions disrupt bacterial enzymes and thus inhibit bacterial growth. The interaction of silver ions with thiol groups (sulfur or —SH groups) in enzymes and proteins is believed to play an essential role in its antimicrobial action. Disruption of critical enzymes and proteins may lead to inhibited cell division, damaged cellular envelopes, and lysing of bacterial cells. Similarly, a high level of hydrogen peroxide has toxic effects. Hydrogen peroxide inhibits bacterial growth by oxidizing cellular components. Reactive oxygen species bind or modify DNA, proteins, and lipids. However, at high concentrations, hydrogen peroxide reduces wound healing by impacting connective tissue formation and wound closure through increases in matrix metalloproteinase levels. An additional obstacle with the use of hydrogen peroxide, is that it is typically used in solutions where it is unstable and difficult to provide a sustained delivery system for broad spectrum antimicrobial use.

For more than 30 years, pressure sensitive adhesives, such as hydrocolloids, have been used for the safe and effective treatment of wounds, as well as the attachment of ostomy devices, catheters, and incontinence devices. Hydrocolloids are occlusive, moisture-retentive dressings that absorb wound exudates, form a gel, and have been shown to have the beneficial effects of reducing the chances of cross-contamination by trapping bacteria within the gel matrix. Adding an antimicrobial agent within the matrix may provide additional bacterial growth control within the dressing to further reduce the incidence of cross-contamination and bioburden within the dressing.

Throughout the last decade, several silver containing pressure sensitive adhesives have been approved and cleared by the FDA, which are comparable to non-antimicrobial devices within these markets. Antimicrobial silver dressings have been repeatedly shown to be safe and effective, regardless of significant potential cytotoxic effects on the wound bed. Nevertheless, over the past few years, silver-based pressure sensitive adhesives have been abandoned due to the high cost of manufacturing, the lack of a higher reimbursement, as well as the potential negative impact on wound healing.

Today, a lack of effective antimicrobial agents within pressure sensitive adhesives creates a significant gap in patient care and poses a threat of serious complications. Caregivers do not have an antimicrobial skin friendly adhesive to aid in advanced wound healing for a patient, or to secure another medical device. Moreover, application of conventional topical antibiotics prior to application of adhesives may be counterindicated or otherwise decrease the effectiveness of the adhesives. An antimicrobial hydrocolloid would minimize the risk of microbial proliferation and cross-contamination.

As noted above, uncontrolled applications of high concentrations of peroxide can be deleterious to a proliferating wound bed. However, a stable hydrogen peroxide that has a controlled release can be used at lower concentrations, while maintaining its antimicrobial efficacy and providing additional benefits. At low concentrations, hydrogen peroxide promotes wound closure, increases the formation of blood vessels, and maintains normal MMP levels. Recent work has demonstrated that hydrogen peroxide can promote neural axon regeneration. After injury of the skin, cells produce hydrogen peroxide to attract neutrophils, which increases neutrophil activity and promotes a healthy wound bed. Studies that remove the low levels of natural hydrogen peroxide in the wound by treating with catalase, show reduced wound healing and reduced blood vessel formation.

The present compositions of antimicrobial pressure sensitive adhesives provide a platform for applications within the medical field to reduce hospital acquired infections, decrease the bioburden under devices attached to the skin, increase the cleanliness of a given therapy, and reduce odor associated with many applications.

Materials that may be used for sequestration of peroxides include any suitable material that may be applied to a subject in need thereof. In one embodiment, superabsorbent materials are contemplated. Contemplated superabsorbent materials (SAMs) include those that are soluble, insoluble, powder-based, film-forming, gel-forming, complexes, copolymers, fibers, etc. Specific SAMs that are contemplated include polyacrylates, alginates, cellulose derivatives (such as carboxylmethycellulose), or any polymer that contains a reactive group that bonds to a peroxide or to another reactive intermediate and forms a bridge with a peroxide containing component. Other reactive intermediates suitable for use in this disclosure include salts or other components or compounds that have the ability to sequester peroxide to the SAMs in a stable composition. Salts suitable for use within this disclosure include, for example, salts of zinc, copper, silver, zirconium, or magnesium.

Useful peroxide sources may include hydrogen peroxide, benzoyl peroxide, or a means for generating peroxide in the form of a stable antimicrobial and immunostimulatory system. For example, a system may include an oxidoreductase enzyme, a substrate for the oxidoreductase enzyme, and other cofactors that lead to the production of a stable peroxide available for sequestration within the adhesive mass prior to or during its manufacture.

Adhesive formulations in this disclosure have numerous applications. For example, adhesive formulations of the present disclosure may be used in conjunction with wound care devices that provide a moist wound healing environment. It is believed that the contemplated hydrocolloids, alginates, foams, and bordered dressings that include a sequestered peroxide compound benefit the patient by reducing the bacterial load and potentially provide additional benefits in healing rates and debridement.

For example, ostomy devices that collect waste and are attached to the body via a contemplated hydrocolloid adhesive would have several patient benefits. These ostomy devices with sequestered peroxide would reduce odor, increase hygiene, and reduce the bacterial and fungal load normally associated with the use of these devices. Thus, one-piece ostomy systems, two-piece collection systems, and urostomy collection systems that include the disclosed adhesive would benefit the patient. In addition to collection devices themselves, additional ostomy accessories such as pastes, sealants, sealing rings, and adhesive strips that include the disclosed adhesive would create a contiguous system that would benefit the user.

In another example, catheters are used to treat medical diseases and are integral components for patient care in clinical/hospital settings. In all cases, traditional adhesive tapes are used to secure catheters to the body. The adhesive disclosed in this application would provide an antimicrobial environment around and over the breeched skin, thus reducing cross infection and potentially life threatening complications. In terms of external catheters and incontinence devices, the disclosed adhesive would provide a clean and hygienic environment to minimize odor and reduce additional damage to the skin with a skin friendly adhesive. Thus, tapes or bandages used to secure these devices could be created with the disclosed adhesives in this application. Specific examples are discussed below in the Examples.

EXAMPLES

Example No. 1

Formulation of a Contemplated Adhesive

Hydrocolloid adhesive formulas are well known, but hydrocolloids that contain antimicrobial agents, astringents, or broad spectrum agents other than silver are not. Typically, hydrocolloid formulations and manufacturing are not compatible with commonly used antimicrobials or broad spectrum agents since they are less stable. Our goal was to develop a hydrocolloid formulation that could employ peroxide as a broad spectrum agent. Given the unstable nature of peroxides, the high molecular weight components within an adhesive, and the temperature profile of a typical manufacturing process, we did not believe that we would be successful.

Hydrocolloid adhesives utilize a continuous phase and discontinuous phase. The continuous phase may contain a mixture of a permanently tacky pressure sensitive adhesive, a styrene-containing thermoplastic elastomer, a liquid rubber, a low molecular weight polyisobutylene, stabilizers, and a low molecular weight liquid polybutene in various amounts and in various combinations. When thermoplastic elastomers are employed as integrating agents, which holds the other high molecular weight components together, high temperatures, in excess of 350° F., are required to meld these components.

The discontinuous phase contains one or more water soluble and/or water swellable absorbent polymers (SAP) such as carboxymethylcellulose (CMC), zinc, hydrocolloid gums, etc. Once the continuous phase is homogenous, then the discontinuous components are added all at once, or in a temporal fashion with corresponding drops in the temperature of the mixture. If the discontinuous phase is too hot, then adding peroxide containing materials could cause an uncontrollable exothermic reaction and lead to the demise of the adhesive and removal of the antimicrobial efficacy.

Suitable thermoplastic styrene-containing elastomers include block copolymers based on styrene-butadiene, styrene-isoprene or styrene ethylene-butylene. Also, a low styrene synthetic copolymer of butadiene and styrene, commonly called SBR rubber, can be used as the thermoplastic elastomer. The elastomer may consist of linear or radial A-B-A block copolymers or mixtures of these A-B-A copolymers with simple A-B block copolymers. The final adhesive composition may contain about 1 wt. % to about 30 wt. % of this component.

Liquid rubbers contemplated herein include synthetic liquid isoprene rubber, hydroxyl terminated synthetic liquid isoprene rubber, hydrogenated liquid isoprene rubber, liquid isoprene-styrene copolymers, liquid isoprene-butadiene copolymers, and liquid butadiene-styrene copolymers. The liquid rubbers typically have a molecular weight of about 25,000 to about 50,000. Preferably, the liquid rubbers have a glass transition temperature of less than about −50° C., and a melt viscosity at 38° C. of from about 500 to about 10,000 poises. Other liquid rubbers known in the art could be useful in the continuous phase. The final adhesive composition should contain about 10 wt. % to about 55 wt. % of these components.

The polyisobutylene component may comprise the Vistanex® LM series of polyisobutylenes, available from Exxon Chemical Corporation, and which have average molecular weights in the range of about 35,000 to about 70,000 and viscosities within the range of about 20,000 to about 140,000 mPa. The low molecular weight polybutene components may comprise the Hyvis series of materials from BP and by the Parapol series of products from Exxon, and may have molecular weights ranging from about 1000 to about 3000. The final adhesive composition should contain about 2 wt. % to about 45 wt. % of these components.

Other ingredients such as a suitable processing stabilizer may also be included in the hot melt adhesive component. Examples include Irganox® 1010, which is pentaerythritol tetrakis (3-(3,5-di-tert-butyl-4-hydroxyphenyl)propionate). Further, tackifiers, oils, and plasticisers may be added to the continuous phase to modify tack and optimize adhesion properties. The final adhesive composition may contain about 0.5 wt. % to about 35 wt. % of these components.

The discontinuous phase may include one or more hydrophilic moisture-absorbing polymers that are swellable in water solutions, including all body secretions. One or more swellable polymers may be present. Suitable swellable polymers include, for example, cross-linked sodium carboxymethyl cellulose or crystalline sodium carboxymethyl cellulose. The swellable polymer may also be a "super absorbent" material such as starch sodium polyacrylate. Suitable water soluble polymers may include sodium carboxymethyl cellulose, pectin, gelatin, guar gum, Arabica gum, locust bean gum, collagen, karaya gum, zinc, metal salts, and starch, and the like. The discontinuous phase should not normally exceed about 65% of the total weight of the adhesive and may be comprised of any combination of soluble and/or insoluble absorbents.

Adhesive compositions may be prepared as follows. The thermoplastic elastomer, polyisobutylenes (PIBs), and the liquid rubber component are blended together in a suitable mixer, normally a sigma blade mixer with an extruder discharge. The mixer is heated to set to 135° C. to 170° C. About 1% of a suitable stabilizer, such as Irganox® 1010, should be added at this stage. Once the thermoplastic elastomer, PIBs, liquid rubbers, and stabilizer blend, the mixer temperature is reduced to 75° C. At specific cooling temperature set points, the oils 135° C. and 110° C., tackifiers 110° C. and 95° C., and plasticizers 105° C. and 90° C. are added in a temporal manner. Once the mix is blended and cooled sufficiently to between about 75° C. and 99° C., the powdery hydrocolloid ingredients, metal salts, peroxide blends, etc. of the discontinuous phase are added to the mixer. We have found that the stabilized combination of SAP, metal salt, and peroxide can be added at a temperature below 99° C. without loss of peroxide antimicrobial activity along with the other discontinuous phase components. These are blended until uniform and the mixer temperature has dropped to about 80° C. At this stage, the fully mixed mass is then removed from the mixer. The mass may be extruded or pressed to the desired thickness while laminating it to suitable substrates to be die cut to shapes, if needed.

Several adhesive formulations that vary in % wt. concentration are represented in Table No. 1 below. It should be noted that these formulations are representative and not inclusive of all envisioned combinations.

TABLE NO. 1

| Component | Peroxide 0.05% | Peroxide 0.1% | Peroxide 0.2% | Peroxide 0.4% | Peroxide 0.8% | Peroxide 2.0% |
|---|---|---|---|---|---|---|
| Thermoplastic Elastomer | 9.00% | 9.00% | 9.00% | 9.00% | 8.00% | 8.00% |
| Rubber | 13.00% | 13.00% | 13.00% | 13.00% | 8.00% | 8.00% |
| AO | 0.50% | 0.50% | 0.50% | 0.50% | 0.50% | 0.50% |
| Tackifier | 5.10% | 5.10% | 5.10% | 5.10% | 5.10% | 5.10% |
| PIB | 22.00% | 22.00% | 22.00% | 22.00% | 33.00% | 33.00% |
| Oil | 12.00% | 12.00% | 12.00% | 12.00% | 8.00% | 8.00% |
| Metal salt peroxide SAP | 0.50% | 1.00% | 2.00% | 4.00% | 8.00% | 20.00% |
| CMC | 32.75% | 32.25% | 31.25% | 29.25% | 29.25% | 17.25% |
| Gelatin | 3.00% | 3.00% | 3.00% | 3.00% | 0.00% | 0.00% |
| Citrus Pectin | 2.00% | 2.00% | 2.00% | 2.00% | 0.00% | 0.00% |
| Zinc Oxide | 0.15% | 0.15% | 0.15% | 0.15% | 0.15% | 0.15% |
|  | 100.00% | 100.00% | 100.00% | 100.00% | 100.00% | 100.00% |

Example No. 2

Antibacterial Efficacy Test for Different Metal Salt Peroxide SAP

In order to confirm the efficacy of the above formulations, we tested each formulation's ability to kill Escherichia coli (E. coli) and MRSA with 1" die cut circles at 30 mil thickness. Each sample was tested against E. coli and MRSA using the agar slurry method. The inoculum level for these samples was higher by 6 logs (seeded at over $1 \times 10^6$ cells per plate).

Subsequently, one 1" adhesive patch (30 mil thick) of each formulation (see Table No. 2) was placed on plates coated separately with E. coli and MRSA to test the zone of inhibition found with each formulation. These tests were incubated at 37° C. for 24 hrs and then photographed. Refer to Table No. 3 below and FIGS. 1A-F and 2A-F for efficacy results against EC and MRSA, respectively.

TABLE NO. 2

| % Active within Adhesive | % Active SAP added |
|---|---|
| A) Peroxide 0.05% | 0.5% active (Mixed SAP with active peroxide, MSPO) |
| B) Peroxide 0.10% | 1% active MSPO |
| C) Peroxide 0.20% | 2% active MSPO |
| D) Peroxide 0.40% | 4% active MSPO |
| E) Peroxide 0.80% | 8% active MSPO |
| F) Peroxide 2.00% | 20% active MSPO |

TABLE NO. 3

|  | Average Log Reduction Overnight | Average Log Reduction t = 0 |
|---|---|---|
| Sample versus EC |  |  |
| A) Peroxide 0.05% | 7.70* ± 0.00 | 6.13* ± 0.00 |
| B) Peroxide 0.10% | 7.70* ± 0.00 | 6.13* ± 0.00 |
| C) Peroxide 0.20% | 7.70* ± 0.00 | 6.13* ± 0.00 |
| D) Peroxide 0.40% | 7.70* ± 0.00 | 6.13* ± 0.00 |
| E) Peroxide 0.80% | 7.70* ± 0.00 | 6.13* ± 0.00 |
| F) Peroxide 2.00% | 7.70* ± 0.00 | 6.13* ± 0.00 |
| Sample versus MRSA |  |  |
| A) Peroxide 0.05% | 5.81* ± 0.00 | 5.76* ± 0.00 |

TABLE NO. 3-continued

|  | Average Log Reduction Overnight | Average Log Reduction t = 0 |
|---|---|---|
| B) Peroxide 0.10% | 5.81* ± 0.00 | 5.76* ± 0.00 |
| C) Peroxide 0.20% | 5.81* ± 0.00 | 5.76* ± 0.00 |
| D) Peroxide 0.40% | 5.81* ± 0.00 | 5.76* ± 0.00 |
| E) Peroxide 0.80% | 5.81* ± 0.00 | 5.76* ± 0.00 |
| F) Peroxide 2.00% | 5.81* ± 0.00 | 5.76* ± 0.00 |

*indicates full kill

As seen in Table No. 3, all samples showed full kill against both MRSA and E. coli.

Figure 3:
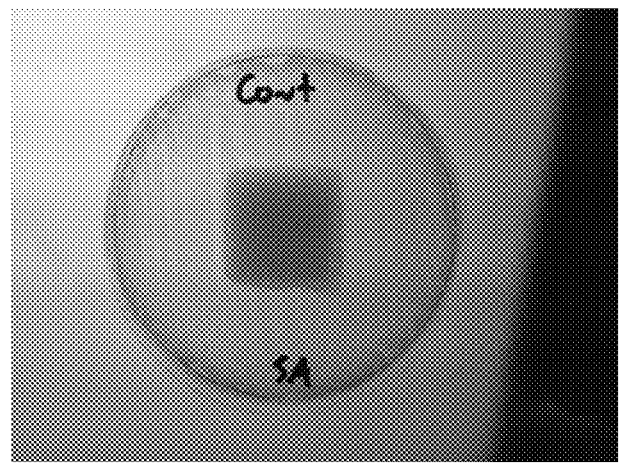
FIG. 3 depicts results of a 1" adhesive patch (30 mil thick) placed on a plate coated with MRSA to test the zone of inhibition caused thereby. The adhesive had no peroxide (control)

The zone of inhibition surrounding the device is attributable to the active MSPO concentration. In contrast, a control with 0% MSPO shown in FIG. 3 exhibited no inhibition of bacterial growth. Moreover, the zones of inhibition of FIGS. 1A-F and 2A-F demonstrate that the different metal salt peroxide SAP formulations not only kill bacteria that they touch, but they further create a zone of protection around a device incorporating the formulations. Thus, devices of the current disclosure incorporating the inventive formulations will provide improved antibacterial functionality to subjects using the devices.

Example No. 3

Description of Creation of a Bandage or Other Device that Includes the Adhesive from Example No. 1

Figure 4:
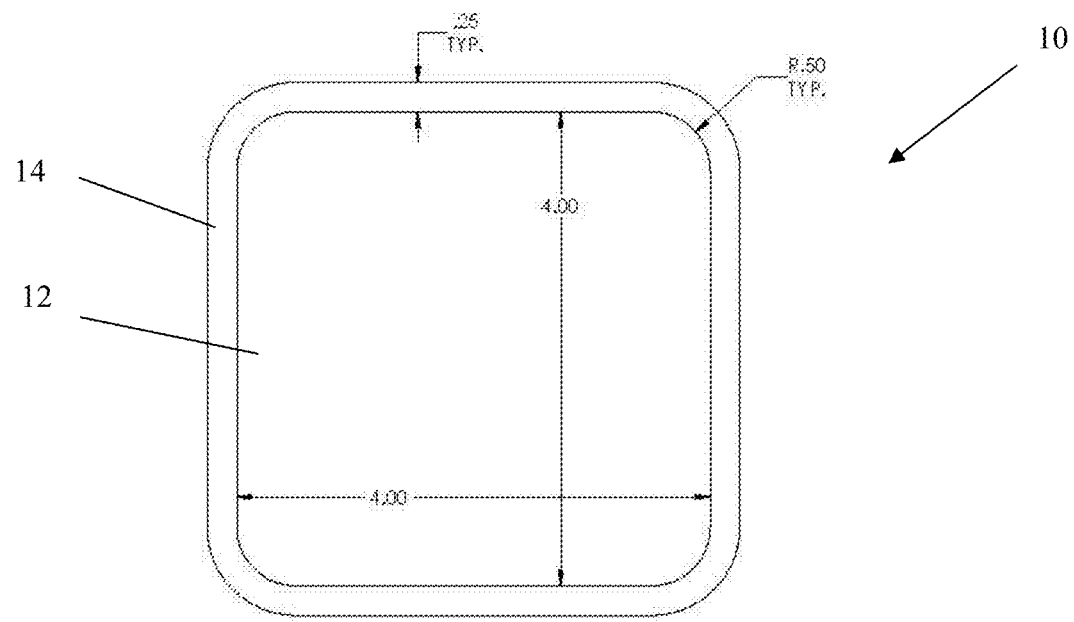
FIG. 4 depicts a device incorporating a metal salt peroxide super absorbent polymer adhesive formulation according to one embodiment.

An example of a contemplated device 10 that includes an adhesive formulation of Example No. 1 is shown in FIG. 4.

The device 10 may include a central portion 12 that may be a sterile gauze-like or other absorptive material made of, for example, a cellulosic or plastic material, and a peripheral portion 14 that may include an adhesive formulation, as described herein. Alternatively, the central portion 12 may constitute the metal salt peroxide SAP formulation and the peripheral portion 14 may be a backing material, such as a cellulosic or plastic material that provides a non-sticky surface. Additional variations are contemplated herein. The device 10 may have any dimensions, such as a square configuration, as shown, or may be rectangular, triangular, oval-shaped, circular, and the like.

Figure 5:
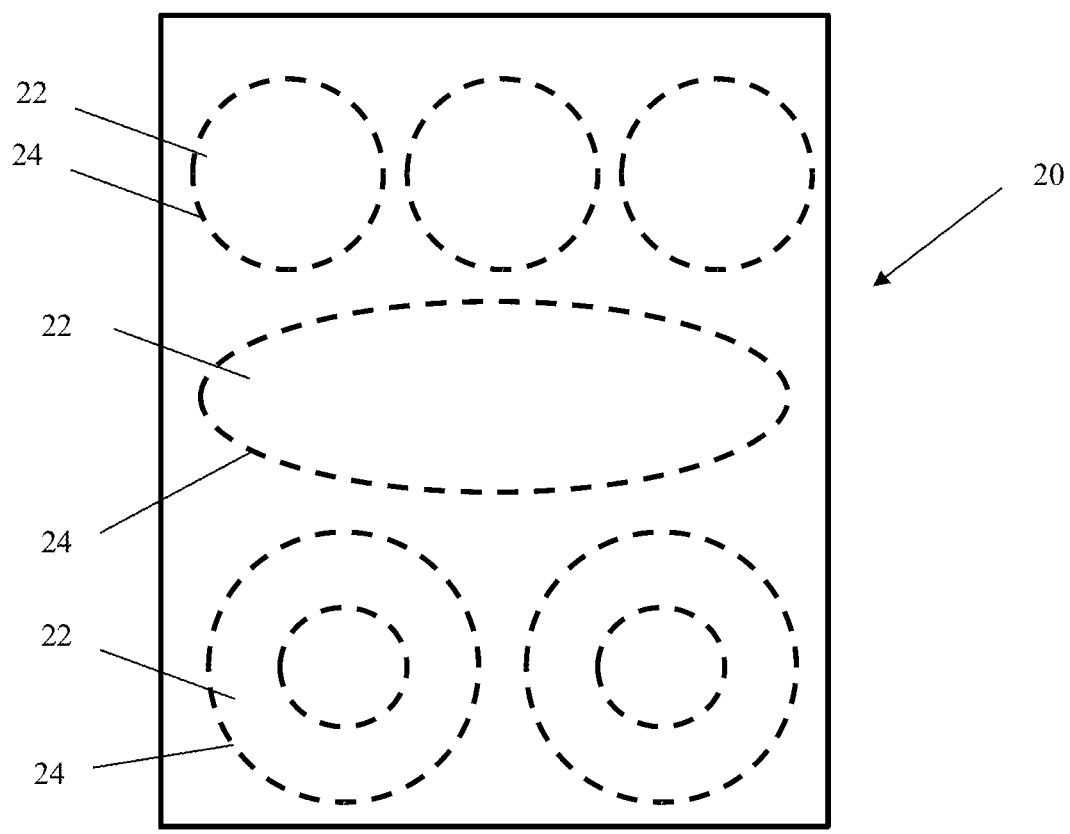
FIG. 5 depicts a blank incorporating a metal salt peroxide super absorbent polymer adhesive formulation according to one embodiment.

It is further envisioned that the device 10 may be custom designed either by a printing and/or automated cutting device into which individualized dimensions for a particular purpose have been programmed via computer or similar interface. Similarly, a blank 20 of the contemplated adhesive material is envisioned, as shown in FIG. 5. The blank 20 may include pre-selected cutouts 22 defined by perforations 24 and be used in various applications depending on the need. Any size and/or shape of blanks 20 and cutouts 22 are contemplated herein. The blank 20 may further include one or two sides (for example, front and back sheets) of non-stick materials to allow sterile handling of the blank prior to use.

INDUSTRIAL APPLICABILITY

The formulations and devices described herein advantageously provide improvements for advanced wound care, incontinence care, catheter securement, and ostomy devices to be attached to a human body through an adhesive.

Numerous modifications will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the application are reserved. All patents and patent publications are incorporated by reference.

I claim:

1. An adhesive device, comprising:
a hydrocolloid adhesive material comprising a super absorbent material chemically bonded either directly or indirectly to a peroxide, wherein the peroxide is stabilized within the hydrocolloid adhesive material and the peroxide is in an amount of 0.05% to 2% by weight within the hydrocolloid adhesive material,
wherein the hydrocolloid adhesive material is prepared by a process comprising the steps of:
mixing one or more components to produce a continuous phase: and
adding a discontinuous phase comprising the peroxide to the continuous phase at a temperature below 99° C.

2. The adhesive device of claim 1, wherein the device is a bandage.

3. The adhesive device of claim 2, wherein the device comprises a non-stick layer on one side thereof.

4. The adhesive device of claim 3, wherein the device comprises a pre-selected cutout having at least one of a square shape, a rectangular shape, a triangular shape, an oval shape, or a circular shape.

5. The adhesive device of claim 1, wherein the super absorbent material is directly bonded to the peroxide.

6. The adhesive device of claim 1, wherein the super absorbent material is indirectly bonded to the peroxide through an intermediate bridge between the super absorbent material and the peroxide.

7. The adhesive device of claim 6, wherein the intermediate bridge is a salt.

8. The adhesive device of claim 1, wherein the discontinuous phase further comprises the super absorbent material and a metal salt.

9. The adhesive device of claim 8, wherein the bond in the adhesive material is an indirect chemical bond between the super absorbent material and the peroxide, wherein the metal salt is an intermediate bridge between the super absorbent material and the peroxide.

* * * * *